(12) United States Patent
Kumar et al.

(10) Patent No.: US 6,218,183 B1
(45) Date of Patent: Apr. 17, 2001

(54) SCREENING METHOD FOR THE IDENTIFICATION OF PLANTS POSSESSING ANTI-MICROBIAL ACTIVITY AND TOLERANCE TO ABIOTIC STRESSES

(75) Inventors: Sushil Kumar, Vikas Nagar; Gurudas Bagchi, Indira Nagar; Mahendra Pandurang Darokar, Aligarij, all of (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/052,823

(22) Filed: Mar. 31, 1998

(51) Int. Cl.[7] ...................................................... C12N 5/04
(52) U.S. Cl. ............................................ 435/420; 424/537
(58) Field of Search ............................. 424/537; 435/420

(56) References Cited

PUBLICATIONS

Kumar, S. et al., Int. J. of Pharmacognosy, vol. 35(3), p. 179–184, Jul. 1997.*
Bagchi, G.D. et al., J. of Medicinal and Aromatic Plant Sciences, vol. 19(4), p. 980–987, Jul. 1997.*
Kumar, S. et al., Current Research on Medicinal and Aromatic Plants, vol. 17(2), p. 177–188, 1995.*
Aswal et al., "Screening of Indian Plants for Biological Activity: Part X", 1984, *Indian J. Exp. Biol.*, 22:312–332.
Bauer et al., "Antibiotic Susceptibility Testing by a Standardized Single Disk Method", 1966, *Am. J. Clin Path.*, 45:493–496.
Bhakuni et al., "Screening of Indian Plants for Biological Activity: Part II", 1969, *Indian J. Exp. Biol.*, 7:250–262.
Bhakuni et al., "Screening of Indian Plants for Biological Activity: Part III", 1971, *Indian J. Exp. Biol.*, 9:91–102.
Bhakuni et al., "Screening of Indian Plants for Biological Activity: Part XIII", 1988, *Indian J. Exp. Biol.*, 26:883–904.
Bhakuni et al., "Screening of Indian Plants for Biological Activity: Part XIV", 1990, *Indian J. Exp. Biol.*, 28:619–637.
Brantner et al., "Antibacterial activity of plant extracts used externally in traditional medicine", 1994, *J. Ethnopharmacology*, 44:35–40.
Dhar et al., "Screening of Indian Plants for Biological Activity: Part I", 1968, *Indian J. Exp. Biol.*, 6:232–247.
Dhar et al., "Screening of Indian Plants for Biological Activity: Part IV",1973, *Indian J. Esp. Biol.*, 11:43–54.
Dhar et al., "Screening of Indian Plants for Biological Activity: Part V", 1974, *Indian J. Exp. Biol.*, 12:512–523.
Dhawan et al., "Screening of Indian Plants for Biological Activity: Part VI", 1977, *Indian J. Exp. Biol.*, 15:208–219.
Dhawan et al., "Screening of Indian Plants for Biological Activity: Part IX", 1980, *Indian J. Exp. Biol.*, 18:594–606.
Grosverhor et al., "Medicinal plants from Riau Province, Sumatra, Indonesia. Part 2: antibacterial and antifungal activity", 1995, *J. Ethnopharmacology*, 45:97–111.
Ieven et al., "Screening of Higher Plants for Biological Activities 1. Antimicrobial Activity", 1979, *Planta Med.*, 36:311–321.
Muanza et al., "Antibacterial and Antifungal Activities of Nine Medicinal Plants from Zaire", 1994, *Int. J. Pharmacology*, 32:337–345.
Taylor et al., "Screening of selected medicinal plants of Nepal for antimicrobial activities", 1995, *J. Ethnopharmacology*, 46:153–159.
Vlietinck et al., "Screening of hundred Rwandese medicinal plants for antimicrobial and antiviral properties", 1995, *J. Ethnopharmacology*, 46:31–47.
Weber et al., "In Vitro Virucidal Effects of *Allium sativum* (Garlic) Extract and Compounds", 1992, *Planta Med.*, 58:417–423.

* cited by examiner

*Primary Examiner*—Jean C. Witz
(74) *Attorney, Agent, or Firm*—Fish & Richardson P.C.

(57) ABSTRACT

A novel screening method for the identification of plants growing on fresh or decomposing bovine cattle dung for antimicrobial activity and tolerance to abiotic stresses.

5 Claims, No Drawings

SCREENING METHOD FOR THE IDENTIFICATION OF PLANTS POSSESSING ANTI-MICROBIAL ACTIVITY AND TOLERANCE TO ABIOTIC STRESSES

FIELD OF THE INVENTION

The present invention relates to a novel screening method for the identification and selection of plants possessing antimicrobial activity and tolerance to abiotic stresses.

BACKGROUND OF THE INVENTION

Many human pathogens have developed resistance against commonly used antibiotics. This has necessitated a search for new anti-microbial substances. Besides other organisms, plants are also considered as a good source of such compounds. So far, known screening methods for testing antimicrobial activities of plants have resulted into identification of very few potential plants. To increase the chances of discovering new antimicrobials from plants, there is a need to develop alternate methods. Plants identified by the method of the present invention have shown high antimicrobial activity and tolerance to various abiotic stresses like high salt concentration, paucity of water etc. These plants can be grown in normally uncultivable lands and may be utilized as the potential source of antibiotics against selected human pathogens.

Antimicrobials have a large market share globally. Extensive screening programs are being carried out throughout the world to identify the potential plant source with new anti-microbial compounds. More than 2800 Indian plant species have so far been screened at random for different biological activities (Dhar et al. 1968, Indian J. Exp. Biol. 6:232; ibid, 1973, Indian J. Exp. Biol. 11:43; ibid, 1974, Indian J. Exp. Biol., 12:512; Bhakuni et al. 1969, Indian J. Exp. Biol. 7:250; ibid, 1971, Indian J. Exp. Biol. 9:91, ibid, 1988, Indian J. Exp. Biol., 26:883; ibid, 1990, Indian J Exp. Biol., 28:619; Dhawan et al., 1977, Indian J. Exp. Biol., 15:208; ibid, 1980, Indian J. Exp. Biol., 18:594, Aswal et al., 1984, Indian J. Exp. Biol., 22:312). However, antimicrobial activity was observed only in 45 plant species (1.6%); among these, 21 species (0.75%) exhibited antibacterial and antifungal activites. Antimicrobial activites were also observed in seeds of 35 species of Angiospems and it was found that only the seeds of 5 species (14%) had this activity. This shows that, the methods of random selection of plants for screening purposes are time consuming and costly. Besides, these offer little chance of discovering a new plant as a potential source of antibiotics (Evans, 1989, Pharmacognosy, ELBS, Bailliere Tindale, London pp. 670).

Another method used commonly for identifying plants with antimicrobial activity is through interpretation of ancient literatures and ethno-botanical data. These are merely confirmation of the activities already mentioned in these literatures. This way of identifying active plants has been moderately successful (Brantner & Grain, 1994, J. Ethnopharmacology, 44:35; Grosverhor et al., 1995, J. Ethnopharmacology, 45:97; Ieven et al., 1979, Planta Med., 36: 311; Taylor et al., 1995, J. Ethnopharmacology, 46:153; Muanza et al., 1994, Int. J. Pharmacology, 32:337; Vlietinck et al., 1995, J. Ethnopharmacology, 46:31; Weber et al., 1992, Planta Med., 58:417).

The common method currently used for testing antimicrobial activity of plant materials is as follows.

Extraction: Powdered plant materials of known quantity are exhaustively extracted with known suitable quantity of methanol either at room temperature for 2–3 weeks or using a Soxhlet extractor for 24 h. The solvent is removed at a low temperature under reduced pressure to yield a thick syrup which is suspended in methanolic water mixture (1:9) and then successively extracted with hexane, chloroform and ethyl acetate. Afforded organic solutions are dried over anhydrous sodium sulfate, filtered and concentrated to give organic extracts. Samples from methanol, hexane, chloroform and ethyl acetate extracts, as well as lyophilized aqueous fractions are further used to test for the antibacterial and antifungal activities (Ieven et al., 1979, Planta Med., 36:311).

Antimicrobial tests: Testing of the antimicrobial activity is usually performed according to the general agar plate diffusion method (Bauer et al., 1966, Am J. Clin Path. 45:493). About 10 mg of plant extract is dissolved in methanol (0.5–1 ml). Sterile blank filter paper discs of 6 mm diameter are impregnated with the resulting solutions and then aseptically deposited on the surface of innoclated plates each containing a specific test microorganism. After 48 hr of incubation at 36° C. for bacteria and 72 hr of incubation at 25° C. for fungi, positive results are established by the presence of clear zones of inhibition around active extracts.

Quantitative estimation of antimicrobial activity: The degree of activity is recorded in four grades according to the internal diameter (in mm) of the zones of the inhibition, incorporating the diameter of the disc (6 m): +3 (strongly active, more than 15 mm of the internal diameter), +2 (moderately active, 14–10 mm of the internal diameter), +1 (less active, internal diameter less than 9 mm) and 0 (inactive). Discs of different concentrations of common antibiotics are used as a positive control (Muanza et al., 1994, Int. J. Pharmacog., 32:337).

DISADVANTAGES OF THE PRIOR ART

The method described above for screening plants for antimicrobial activity is lengthy, time consuming and costly on account of the use of different solvents for extraction of plant materials. On the other hand, the present screening procedure for identifying potent antimicrobial plant/plant parts is quick as extraction process/procedure is completely deleted, involves less chemicals and is almost certain with reliability. The plants identified so far by this method have exhibited 100% activity and many of them are new records. These findings may lead to the discovery of new chemical agents with microbial activity which are not yet discovered. These plants are also tolerant to abiotic stresses and can be grown/cultivated in any drought prone and/or saline soils.

OBJECTS THE INVENTION

The main object of the present invention is to develop a novel screening process for the identification and selection of plants possessing antimicrobial activity and tolerance to abiotic stresses.

Another object of the present invention is to provide an improved, reliable and accurate quantitative estimation method to determine the antimicrobial potential of seeds/plant parts using them directly in measured quantities, instead of their extracts.

SUMMARY OF THE INVENTION

The above-objects are achieved by providing a novel screening process for the identification and selection of plants possessing high antimicrobial activity and tolerance to abiotic stresses; which comprises identification of plant species that grow naturally and survive on the fresh/decomposing (10–15 days old) cattle dung, a medium rich in different microbes and high salt concentration; testing of their seeds against selected microbes directly in measured quantities, eliminating the extraction process completely; quantitative estimation of antimicrobial potency using the radius of inhibition zone as well as the ratio of inhibition zone and weight of the tested seed; calibration of antimicrobial potency of seeds with known antibiotics and assessment of their salt tolerant capability. The same applies to the other organs of the plant eg. root, stem, leaf, flower and fruit.

DESCRIPTION OF THE INVENTION

In India, decomposed cattle dung is commonly used as organic manure for garden and farm plants. However, it is found that several medicinal, aromatic and horticultural plants when grown in pots containing mixture of fresh cattle dung and soil, do not survive. It is further observed that upon deposition of cattle dung, small herbaceous plants decay rapidly and often die. The area outside the dung patch gets rapidly covered by grass, while the dung patch itself remains unpopulated or is sparsely populated by grasses for many months. This shows that fresh or decomposing cattle dung is a harsh and unsuitable medium for plant growth. A majority of the seeds are not able to produce seedlings on it. The dung excreted by cattle is a complex substance, rich in organic matter and salts. The organic matter consists of cellulose, lignin and hemicellulose, products of animal metabolism, a large a varied population of micro-organisms and their metabolites. The micro-organisms in the dung include those which are excreted by the animal in the faeces and those that colonize in the dung from the environment. A variety of bacteria, actinomycetes, fungi and protozoa comprise the micro flora of the dung. These include organisms that are saprophytic and pathogenic to animals and/or plants. In the process of decomposition, a series of physical and chemical changes occur. Microorganisms responsible for the decomposition utilize the organic matter as the source of carbon to generate energy and in the process, temperature of the dung medium may rise to as high as 40°–60° C. and a variety of secondary metabolites such as antibiotics and toxins are liberated into the dung. The factors that do not permit germination of plant seeds and growth of seedlings on cattle dung undergoing microbial decomposition, include hyperthermia due to microbial respiration, growth inhibitors secreted by microorganisms and the high salinity due to high concentration of total soluble salts (4.5–5.4 dSm$^{-1}$). As the cattle dung decomposes, there is loss mainly to the carbonaceous portion, excess salts leach out due to various environmental factors and the microbial activity also recedes. This makes the cattle dung manure, suitable for plant growth. (Kumar et al. 1995, Curr. Res. on Med. and Arom. Plants, 17:177). In spite of the harsh conditions of fresh cattle dung, we have observed some plant species to grow on them without showing any adverse effect. These plants were termed as coprophilous (Kopros dung; philein-to love). It appears that the seeds and seedlings of coprophilous plants are salt tolerant and also tolerant to the attack of different microbes present in the cattle dung. The potential of the seeds of coprophilous plants as a possible source of antibiotics have been examined here along with their salt tolerance capacity.

The invention relates to a novel screening method for the identification of plants growing on fresh or decomposing (10–15 days old) bovine cattle dung for antimicrobial activity and tolerance to abiotic stresses comprising the steps of:

a) isolating plant species growing naturally and surviving on the fresh or decomposing (up to 15 days old) bovine cattle dung;

b) planting the isolated plant species from step (a) above and growing them to maturity.

c) identifying the matured plant species obtained from step (b) above;

d) collecting the seeds from the identified plant species obtained in step (c) above;

e) measuring the weight of the seeds obtained from step (d) above for quantification of antimicrobial activity;

f) sterilising the isolated seeds obtained in step (d) above;

g) preparing the nutrient medium for bacterial and fungal cultures;

h) inocculating the bacterial and fungal strains in the nutrient medium prepared in step (g) above;

i) deposition of seeds isolated in step (f) above in the inocculated culture medium containing different microbial strains;

j) incubating a set of test plates with seeds on culture medium containing bacterial strains for about 24 hrs at 37° C.;

k) incubating a different set of test plates with seeds on culture medium containing fungal strains for about 42 hrs at 28° C.;

l) testing the incubated test plates from steps (J&K) above for antimicrobial potency by measuring the radius of inhibition and calculating the ratio between the radius of inhibition zone and weight of seed;

m) repeating steps (g) to (l) above at least three times to confirm the enhanced antimicrobial activity of isolated seeds with the normal seeds inocculated in same manner as given in step (f) to (k) above which showed similar antimicrobial activity in the test seeds as well as normal seeds indicating thereby the inherent antimicrobial character in the plant species so identified obtained from sources other than cattle dung;

n) repeating steps (g) to (l) with filter paper discs carrying different amounts of antibiotics instead of seeds to compare the antimicrobial potency (radius of inhibition zone) of the seeds of coprophilous species with known antibiotics, and o) testing the seeds obtained from step (d) to measure the ability to grow under abiotic stresses such as salt concentrations by germinating them in different concentrations of NaCl.

Accordingly, the seeds of coprophilous plants growing in bovine cattle dung (fresh or decomposing upto 15 days old) identified for antimicrobial potency and abiotic stress are: *Alysicarpus vaginalis, Amaranthus gracilis, A. spinocus, Anethum sowa, Blumea lacera, Brassica campestris, Bryonia laciniosa, Carica papaya, Commelina haeskerlii, Corchorus aestuans, C. olitorius, Chenopodium album, C. ambrosoides, Cucumis melovar. utilissimus, Cucurbita maxima, Cyperus rotundus, Datura metel, Daucus carota, Digera muricata, Dactyloctenium aegyptium, Echinochloa colonum, Ficus glomerata, F. infectoria, Glinus oppositifolia, Ipomea pestigridis, Jussia subfruticosa, Lagenaria siceraria, Lindernia parviflora, Malvastrum coromandelianum, Melochia corchorifolia, Murdania nudiflora, Oldenlandia corymbosa, Oplismanus burmanii, Parthenium hysterophorus, Peristrophe bicalyculata, Phyllanthus amarus, Phyllanthus fraternus, Physalis minima, Portulaca oleracea, Rungia repens, Raphanus sativus, Sesbania cannabina, Setaria glauca, Sida rhombifolia, Sorghum halepense, Triumfetta rhomboidea, Trianthema portulacastrum, Vigna unguiculata, Xanthium strumarium, Zea mays* etc.

The plant seeds selected by the present method are directly used for testing the antimicrobial property. In fact, the present screening method obviates the steps of solvent extraction of plant material and drying step resulting in substantial saving in screening time of at least 7 days.

The significance of these findings are illustrated by the following examples which should not be constructed to limit the scope of the present invention.

EXAMPLE 1

To identify the coprophilous plants with antimicrobial activity 200 randomly chosen plants from fresh/decomposing, 10–15 days old cattle dung heaps were examined in each month from August to October, 1996 around Lucknow city. The plants were botanically identified. Some of the herbaceous species were transferred from the dung heaps to pots to obtain their seeds for testing of antimicrobial activity. Seeds of the tree species were collected from the plants growing naturally in the study area.

The purpose of carrying out the survey of cattle dung heaps in the rainy months from August to October was that, during this period, the dung heaps are usually not disturbed and the surface remains soft, bearing ample moisture to facilitate seed lodging and germination. Seeds of 50 common coprophilous plants were tested for their antimicrobial activity. Some of the plant species tested are shown in table 1.

EXAMPLE 2

Seeds were directly used to measure the antimicrobial activity instead of their extracts as used commonly. As the seeds/seed parts of different plant species are not of same size and shape, the usual method of measuring diameter of inhibition zone (including disc) was suitably modified. Following two new methods were used.

A. To quantify the antibacterial activity, the distance between the outer boundaries of the seed/seed fragments and the zone of bacterial growth inhibition (radius) is measured at several points.

B. To compare the antibacterial activities between the seeds of different weights/sizes, the ratio between the width of bacterial growth inhibition zone produced by a particular seed and its weight (IZ/SW) gives a measure of activity in 1 mg of seed material.

These methods can also be applied to measure the antimicrobial activities of different plants parts.

EXAMPLE 3

The bacterial strains used for testing our claim for antibacterial activity were those of *Bacillus subtilis* (MTCC-121), *Pseudomonas chichorii* (PC-1) and *Salmonella typhimurium* (NMFT3). The antibacterial tests were conducted using 10 cm diameter petridishes containing sterile solid media. The solid culture medium used for *B. subtilis* was *Luria agar* containing bactotryptone 10 g/l, yeast extract 5 g/l, Nacl 10 g/l and 1.5% agar. The Difco nutrient agar was the medium used for *P. cichorii* and *S. typhimurium*. To obtain cultures, the bacteria were inoculated into the nutrient broth and incubated at 37° C. in water bath shaker. Whole seed or seed fragments were surface sterilized with 0.1% mercuric chloride for 2 min. and then washed 3 times with sterile distilled water. The seeds were dried on sterile filter papers and placed on nutrient agar plates previously seeded with $10^7$ to $10^8$ cells of the test bacteria. The test plates were incubated at 37° C. for 24 hr. Antibacterial activities of the 50 examined coprophilous species have been shown in Table 1.

EXAMPLE 4

The fungal strains used for testing our claim for antifungal activity were those of *Fusarium moniliforme* (GRM-102), *Aspergillus awamori* (AAS-4) and *Trichoderma viridis* (TVS-1). Fungal cultures were grown on potato dextrose agar (PDA) at 28° C. for 7 days. Suspension of fungi were prepared in 0.85% normal saline solution containing 0.1% Tween 80. The turbidity of suspension for inoculum was adjusted to the McFarland No. 0.5 turbidity standard. Seeded agar plates were prepared by pouring 20 ml of PDA into each plate. After solidification of medium, each plate was overlaid with 3 ml of PDA containing 0.1 m of inoculm by first cooling the medium (PDA) to 50° C. and maintaining them at that temperature in a water bath. Inoculum (0.1 ml) was added asceptically, swirled and the contents (3.1 ml) was immediately poured into PDA surface. The plates were slightly tilted to and for once for even spreading. The test plates were incubated at 28° C. for 42 hr. Antifungal activities of 50 examined coprophilous species have been shown in Table 1.

EXAMPLE 5

Antimicrobial activity of the seed of 50 coprophilous species were examined. Results are shown in table 1. Interestingly, all of the tested species exhibited antimicrobial activity against one or the other test bacteria or fungi. However, the seeds of *Datura metel* and *Oldenlandia corymbosa* exhibited highest antimicrobial activity on the basis of width of inhibition zone produced and IZ/SW ratio respectively. In our view the seeds which are minute and exhibited good activity on the basis of IZ/WS ratio are the source of more powerful antimicrobial compounds.

EXAMPLE 6

The filter paper discs carrying different amounts of antibiotics (streptomycin, tetracyclin, chloramphenicol for bacteria and Amphotericin, Bavastin and Griesofulvin for fungi) were used as positive controls to measure the strength of antibacterial/antifungal activity of the seeds. The seeds of the plant *Ammania baccifera* (Lythraceae) which was common in the study area but never found to occur on the cattle dung heaps were used as normal control (Table 2 & 3). Interestingly, seeds of this species exhibited very little activity against few of the test organisms. This showed that the seeds of coprophilous plants possess antimicrobial compounds to protect itself from the possible attack of various microorganisms present on the decomposing/fresh cattle dung. Such high percent. (>90%) of active plants/parts was never observed in any of the previous work under taken so far.

EXAMPLE 7

Seeds of coprophilous plants such as *Sorghum halepense* and *Brassica campestris* were germinated in different concentrations of NaCl (0.01 M to 0.5 M) to test their salt tolerance ability as compared to the seeds of normal species like *B. oleracea var. botrytis* and *Trigonella foenumgraecum* at 25° C. and 80% humidity conditions. Interestingly both the coprophilous species tolerated salt concentration upto the level of 0.2 M, while the seedlings of normal plants died at this concentration. (Table 4). This shows that the coprophilous plants are also able to tolerate various abiotic stresses like high salt concentrations etc and are useful for growing them in waste lands for soil reclaimation.

The present invention shows that the seeds of plant species, which germinate and survive on the fresh/ decomposing cattle dung, infested with different types of microorganisms, possess capability to protect itself from the microbial attack and will prove a good source of new antimicrobial compounds, chances of finging antimicrobial activity in the seeds of coprophilous plants are very high (90–100%) as compared to the seeds of normal plants (14%). Among the examined 50 coprophilous plants, plant parts other than seeds of 30 species were tested for antimicrobial activites (Dhar et al. 1968, 1973, 1974; Bhakuni et al. 1969, 1971, 1988, 1990; Dhawan et al. 1977, 1980; Aswal et al. 1984; Kumar et al. 1995), about 50% of the test plants exhibited antimicrobial activity. This shows that chances of finding antimicrobial activity in coprophilous plants/parts are also high. It was observed that the plant species which occurred more frequently on this medium possessed higher level of antimicrobial activity (Table 1). The coprophilous plants possessing minute seeds are particularly important because most of them show high antimicrobial activity on the basis of IZ/WS ratio and appear to be the source of more powerful antimicrobial compounds. The coprophilous plants also show tolerance to high salt concentrations. The level of tolerance of the species to different stresses will vary according to their genotypes. In this way, we have for the first time developed a novel screening method to identify plants that are tolerant to biotic and abiotic stresses.

The biotic stresses include infectious agents of various kinds and the abiotic stresses include the physiochemical stresses like high salt concentration, paucity of water etc. We have also discovered that the seeds of these plants are good source(s) of antimicrobial compounds.

The main advantages of the present invention are
1. This screening method for identifying plant species with antimicrobial activity is quick and cheap as solvent extraction process/procedure is completely deleted.
2. Chances of discovering potential plants with antimicrobial compounds are high (<90%) as compared to the existing methods (0.5–2.0% by random selection).
3. The use of ratio of inhibition zone and weight of seeds (IZ/WS) or any plant parts is an accurate, reliable and novel method for quantitative estimation of the antimicrobial potentials of plant materials of variable sizes.
4. This invention may lead to the discovery of novel antimicrobial compounds.

TABLE 2

Inhibition of the bacterial growth produced by the varying amounts of certain common antibiotics.

| Si. Antibiotics/ No. seed | Amount ($\mu$g/ml) of antibiotic in the filter paper disc of 6 mm diameter | Radius (mm) of the inhibition zone produced on the test bacteria | | |
|---|---|---|---|---|
| | | Baciilus subtilis | Pseudomonas cichori | Salmonella typhimorium |
| 1. Streptomycin | 1 | 2.0 | 8.6 | 1.8 |
| | 5 | 6.0 | 3.5 | 5.0 |
| | 10 | 8.0 | 5.5 | 8.0 |
| | 15 | 10.0 | 7.8 | 6.5 |
| 2. Tetracyclin | 1 | 7.0 | 2.0 | 8.0 |
| | 5 | 9.0 | 4.0 | 7.0 |
| | 10 | 11.0 | 5.5 | 9.0 |
| | 15 | 13.0 | 8.0 | 11.0 |
| 3. Chloramphenicol | 1 | 0.2 | 0 | 0 |
| | 5 | 1.5 | 8.2 | 5.0 |
| | 10 | 8.0 | 8.6 | 6.0 |
| | 15 | 10.0 | 1.0 | 8.0 |
| Ammonia baccilera (tythracene) Non coprophilous plant (Normal control) | — | 0.1 | 0 | 0 |

TABLE 3

Inhibition of fungal growth produced by the varying amounts of certain common antibiotics.

| Si. Antibiotics/ No. seeds | Amount ($\mu$g/ml) of antibiotic in the filter paper disc of 6 mm diameter | Radius (mm) of the inhibition zone | | |
|---|---|---|---|---|
| | | Fusarium moniliforme | Aspergillus swamori | Trichoderm viridis |
| 1. Amphotericin | 10.0 | 4.0 | 9.0 | 0 |
| | 1.0 | 1.0 | 2.0 | 0 |
| | 0.1 | 0.0 | 0.0 | 0 |
| 2. Bevastin | 10.0 | 2.0 | 5.0 | 3.0 |
| | 1.0 | 0.0 | 1.0 | 2.0 |
| | 0.1 | 0.0 | 0.0 | 0 |
| 3. Griesofulvin | 10.0 | 0 | 0 | 0 |
| | 1.0 | 0 | 0 | 0 |
| | 0.1 | 0 | 0 | 0 |

TABLE 3-continued

Inhibition of fungal growth produced by the varying amounts of certain common antibiotics.

| Si. Antibiotics/ No. seeds | Amount (μg/ml) of antibiotic in the filter paper disc of 6 mm diameter | Radius (mm) of the inhibition zone | | |
|---|---|---|---|---|
| | | *Fusarium moniliforme* | *Aspergillus swamori* | *Trichoderm viridis* |
| Seed of *Ammonia baccifera* (Lytheraceae) non coprophilous plant (normal control) | | 0 | 0 | 0 |

TABLE 4

Effects of different salt concentrations on the seed germination (%) and seedling growth (%) in some caprophilous and non-caprophilous species in relation to their control plants grown in distilled water.

| | Caprophilous species | | | | | | Non-caprophilous specices | | | | | |
|---|---|---|---|---|---|---|---|---|---|---|---|---|
| | *Sorghum halepense* | | | *Brassica campestris* | | | *Brasica aleracea* var. *botrytis* | | | *Trigonella foenum-graecum* | | |
| Treatment [NaCl concentrations) | Germination (%) | Shoot length (%) | Root length (%) | Germination (%) | Shoot length (%) | Root length (%) | Germination (%) | Shoot length (%) | Root length (%) | Germination (%) | Shoot length (%) | Root length (%) |
| 0.01 n. | 128 | 189 | 129 | 112 | 130 | 132 | 225 | 192 | 94 | 100 | 248 | 266 |
| 0.02 n. | 86 | 87 | 122 | 186 | 85 | 99 | 200 | 184 | 59 | 98 | 214 | 241 |
| 0.05 n. | 71 | 77 | 115 | 100 | 63 | 52 | 150 | 96 | 53 | 88 | 93 | 225 |
| 0.1 n. | 57 | 55 | 66 | 94 | 61 | 41 | 125 | 65 | 47 | 70 | 99 | 141 |
| 0.2 n. | 43 | 25 | 33 | 88 | 33 | 38 | 25 | 8 | 35 | 0 | NA | NA |
| 0.5 n. | 14 | 1 | 4 | 58 | 7 | 3 | 8 | NA | NA | 8 | NA | NA |

NA = Not applicable

TABLE 1

Inhibition of the microbial growth by the seeds or seed fragments of certain angiospermous plants.

| S. No. | Plant species (family) | Frequency of occurrence on 200 heaps. (%) | Mean weight (mg) of the whole seed (w) or seed fragment (f) tested | Inhibition of the bacterial and fungal growth measured by the parameters: Width of the inhibition zone; ratio of the inhibition zone (mm) and weight of seeds or its fragments (mg) in parenthesis | | | | | |
|---|---|---|---|---|---|---|---|---|---|
| | | | | *1 | 2 | 3 | 4 | 5 | 6 |
| 1. | Alysicarpus vaginalis Papilionaceae (CIMAP 5825) | 0.5 | 2.0 (w) | 1.0 (0.5) | 0.8 (0.4) | 0.5 (0.25) | 1.5 (0.75) | 1.0 (0.5) | 0 |
| 2. | Amaranthus gracilis Amaranthaceae (CIMAP 6282) | 10.0 | 0.4 (w) | 1.0 (2.5) | 0 | 0 | 0 | 0.5 (1.2) | 0 |
| 3. | Amaranthus spinosus Amaranthaceae (CIMAP 5874) | 0.5 | 0.26 (w) | 1.0 (3.8) | 0 | 0 | 0 | 0 | 0 |
| 4. | Anethum sowa Apiaceae (CIMAP 4312) | 0.5 | 1.4 (w) | 0 | 4.0 (2.8) | 5.3 (3.78) | 7.0 (5.0) | 1.5 (1.07) | 0 |
| 5. | Blumea lacera Asteraceae (CIMAP 6280) | 0.5 | 0.03 (w) | 0 | 0 | 0.5 (16.6) | 0 | 0 | 0 |
| 6. | Brassica campestris var. yellow | 3.0 | 4.8 (w) | 1.5 (0.3) | 0 | 0.2 (0.04) | 1.5 (0.3) | 1.1 (0.2) | 0 |
| | var. brown Brassicaceae (CIMAP 5825) | 12.0 | 4.8 (w) | 2.5 | 1.6 (0.5) | 2.5 (0.3) | 4.5 | 0 (0.9) | 0 |
| 7 | Bryonia laciniosa Cucurbitaceae (CIMAP 5863) | 0.5 | 18.0 (w) | 0.6 (0.02) | 2.5 (0.13) | 1.2 (0.06) | 1.5 (3.0) | 0 | 0 |
| 8. | Carica papaya Caricaceae (CIMAP 9227) | 1.0 | 14.0 (w) | 2.0 (0.14) | 2.3 (0.16) | 0.2 (0.011) | 7.5 (0.5) | 3.5 (0.25) | 1.0 (0.07) |
| 9. | Commelina haeskerlii Commelinaceae (CIMAP 6294) | 1.0 | 3.7 (w) | 1.8 (0.48) | 5.0 (1.35) | 2.6 (0.702) | 4.5 (1.2) | 4.2 (1.13) | 2.1 (0.56) |
| 10. | Corchorus aestuans Tiliaceae (CIMAP 3935) | 2.0 | 0.8 (w) | 1.0 (2.25) | 1.0 (1.25) | 2.0 (2.5) | 2.0 (2.5) | 0.5 (0.6) | 0 |
| 11. | Corchorus olitorius Tiliaceae (CIMAP 5907) | 2.0 | 1.5 (w) | 2.0 (1.3) | 1.6 (1.0) | 1.5 (1.0) | 3.5 (2.3) | 2.0 (1.3) | 0 |
| 12. | Chenopodium album Chenopodiaceae (CIMAP-5733) | 2.0 | 0.2 (w) | 1.0 (5.0) | 0 | 0 | 2.0 (10.0) | 0.4 (2.0) | 0 |
| 13. | Chenopodium ambrosiodes Chenopodiaceae (CIMAP-5756) | 0.5 | 0.2 (w) | 0 | 0 | 0 | 1.8 (9.0) | 0 | 0 |
| 14. | Cucumis melo var utilissimus Cucurbitaceae (CIMAP-6241) | 11.0 | 17.0 (w) | 0 | 2.0 | 3.0 | 2.0 | 2.5 | 0 |
| 15. | Cucurbita maxima Cucurbitaceae (CIMAP 9240) | 3.0 | 5.1 (f) | 0.5 (0.09) | 3.6 (0.7) | 2.7 (0.529) | 7.5 (1.47) | 2.0 (0.39) | 0 |
| 16. | Cyperus rotundus Cyperaceae (CIMAP 6379) | 16.0 | 0.1 (w) | 1.3 (13.0) | 0.5 (5.0) | 2.1 (21.0) | 1.5 (15.0) | 2.0 (20.0) | 0 |
| 17. | Datura metel Solanceae (CIMAP 6530) | 0.5 | 11.4 (w) | 1.6 (0.13) | 3.5 (0.3) | 2.3 (0.2) | 7.6 (0.6) | 6.6 (0.5) | 0 |
| 18. | Daucus carota Apiaceae (CIMAP 9235) | 0.5 | 2.5 (w) | 2.0 (0.8) | 1.7 (0.68) | 1.8 (0.72) | 4.5 (1.8) | 1.4 (0.5) | 0 |
| 19. | Digera muricata Amaranthaceae (CIMAP 3876) | 3.0 | 2.2 (w) | 2.0 (0.9) | 1.6 (0.7) | 3.6 (1.63) | 2.7 (1.2) | 2.0 (0.9) | 0 |
| 20. | Dactyloctenium aegyptium Poaceae (CIMAP 6134) | 4.0 | 0.2 (w) | 0 | 0.8 (4.0) | 0 | 2.5 (12.2) | 0 | 0.5 (2.5) |
| 21. | Echinochloa colonum Poaceae (CIMAP 4221) | 1.0 | 1.0 (w) | 1.0 (1.0) | 1.0 (1.0) | 1.8 (1.8) | 0 | 2.0 (2.0) | 0 |
| 22. | Ficus glomerata Moraceae (CIMAP 6547) | 2.0 | 0.2 w) | 0.5 (2.5) | 1.0 (5.0) | 1.2 (6.0) | 1.5 (7.5) | 2.2 (11.0) | 0.5 (2.5) |
| 23. | Ficus infectoria Moraceae | 4.0 | 0.4 (w) | 0 | 0.8 (2.0) | 0.2 (0.5) | 2.0 (5.0) | 0 | 0 |

TABLE 1-continued

Inhibition of the microbial growth by the seeds or seed fragments of certain angiospermous plants.

| S. No. | Plant species (family) | Frequency of occurrence on 200 heaps. (%) | Mean weight (mg) of the whole seed (w) or seed fragment (f) tested | Inhibition of the bacterial and fungal growth measured by the parameters: Width of the inhibition zone; ratio of the inhibition zone (mm) and weight of seeds or its fragments (mg) in parenthesis | | | | | |
|---|---|---|---|---|---|---|---|---|---|
| | | | | *1 | 2 | 3 | 4 | 5 | 6 |
| 24. | Glinus oppositifolia Aizoaceae (CIMAP 6275) | 0.5 | 0.02 (w) | 1.0 (50.0) | 0 | 0 | 0 | 0 | 0 |
| 25. | Iopmoea pestigridis Convolvulaceae (CIMAP 6203) | 1.0 | 12.5 (w) | 1.0 (0.08) | 1.4 (0.11) | 1.4 (0.112) | 0 | 0 | 0 |
| 26. | Jussiaea subfruticosa Onagraceae (CIMAP 3752) | 0.5 | 0.05 (w) | 1.0 (20.0) | 0.7 (14.0) | 0.5 (10.0) | 2.0 (40.0) | 0.8 (16.0) | 0 |
| 27. | Lagenaria siceraria Cucurbitaceae (CIMAP 9230) | 2.0 | 0.9 (w) | 0.5 (0.5) | 3.0 (3.3) | 2.4 (2.6) | 3.0 (3.3) | 3.5 (3.8) | 0 |
| 28. | Lindernia parviflora Scrophulariaceae (CIMAP 6268) | 0.5 | 0.04 (w) | 0.8 (20.0) | 0.3 (7.5) | 0 | 0 | 0 | 0 |
| 29. | Malvastrum coromandelianum Malvaceae (CIMAP 6111) | 0.5 | 0.8 (w) | 1.8 (2.2) | 4.0 (5.0) | 2.3 (2.8) | 4.0 (5.0) | 3.0 (3.7) | 1.8 (2.2) |
| 30. | Melochia corchorifolia Sterculiaceae (CIMAP 3005) | 2.0 | 3.0 (w) | 1.5 (0.5) | 1.6 (0.5) | 0 | 4.7 (1.5) | 3.5 (1.1) | 0 |
| 31. | Murdania nudiflora Commelinaceae (CIMAP 6138) | 3.0 | 0.4 (w) | 2.0 (5.0) | 3.0 (7.5) | 2.0 (5.0) | 2.2 (5.5) | 3.2 (8.0) | 2.0 (5.0) |
| 32. | Oldenlandia corymbosa Rubiaceae (CIMAP 5772) | 0.5 | 0.03 (w) | 0.8 (26.6) | 0 | 0.3 (10.0) | 0.8 (26.6) | 0.2 (6.6) | 1.0 (33.3) |
| 33. | Oplismenus burmannii Poaceae (CIMAP 6477) | 1.0 | 0.5 (w) | 1.5 (3.0) | 0 | 0.5 (1.0) | 2.0 (4.0) | 0 | 0 |
| 34. | Parthenium hysterophorus Asteraceae (CIMAP 6393) | 4.0 | 0.5 (w) | 1.0 (1.8) | 3.2 (5.8) | 2.6 (5.2) | 5.5 (11.0) | 2.5 (5.0) | 0 |
| 35. | Peristrophe bicalyculata Acanthaceae (CIMAP 6088) | 1.0 | 0.9 (w) | 3.0 (3.3) | 2.8 (3.1) | 4.0 (4.4) | 0 | 1.5 (1.6) | 0 |
| 36. | Phyllanthus amarus Euphorbiaceae (CIMAP 6589) | 1.0 | 0.16 (w) | 1.0 (6.25) | 3.2 (20.0) | 1.0 (6.25) | 2.0 (12.5) | 1.0 (6.25) | 0 |
| 37. | Phyllanthus fraternus Euphorbiaceae | 6.0 | 0.17 (w) | 1.6 (8.8) | 2.0 (11.7) | 1.5 (8.8) | 0.5 (2.9) | 1.8 (10.5) | 0 |
| 38. | Physalis minima Solanceae (CIMAP 6259) | 12.0 | 0.7 (w) | 3.0 (4.2) | 2.0 (2.8) | 2.3 (2.28) | 2.7 (3.8) | 1.2 (1.7) | 0 |
| 39. | Portulaca oleracea Portulacaceae (CIMAP 5972) | 6.0 | 0.17 (w) | 1.0 (5.8) | 0 | 0.5 (2.94) | 1.1 (6.4) | 0.75 (4.4) | 0 |
| 40. | Rungia repens Acanthaceae (CIMAP 6194) | 0.5 | 0.14 (w) | 0.5 (3.5) | 2.0 (14.2) | 0 | 1.5 (10.7) | 0.5 (3.5) | 0 |
| 41. | Raphanus sativus Brassicaceae (CIMAP 9231) | 3.0 | 10.47 (w) | 1.0 (0.09) | 2.0 (0.19) | 1.3 (0.124) | 3.7 (0.35) | 1.6 (0.15) | 0 |
| 42. | Sesbania canabina Papilionaceae (CIMAP 9229) | 4.0 | 17.5 (w) | 1.0 (0.05) | 1.0 (0.05) | 1.6 (0.91) | 4.0 (0.22) | 1.0 (0.05) | 0 |
| 43. | Setaria glauca Poaceae (CIMAP 4278) | 1.0 | 0.6 (w) | 2.0 (3.3) | 0.3 (0.5) | 0.5 (0.83) | 2.0 (3.3) | 3.5 (5.8) | 2.0 (3.3) |
| 44. | Sida rhombifolia Malvaceae (CIMAP 6503) | 0.5 | 2.6 (w) | 3.0 (1.2) | 1.8 (0.7) | 2.0 (0.8) | 2.2 (0.84) | 2.2 (0.84) | 2.0 (0.8) |
| 45. | Sorghum halepense Poaceae (CIMAP 4242) | 0.5 | 3.8 (w) | 2.8 (0.7) | 0.5 (0.13) | 2.0 (0.526) | 3.5 (0.9) | 3.5 (0.9) | 0 |
| 46. | Triumfetta rhomboidea Tiliaceae (CIMAP 6172) | 0.5 | 15.6 (w) | 2.0 (0.12) | 2.2 (0.14) | 5.0 (0.3) | 5.5 (0.35) | 1.0 (0.06) | 0 |
| 47. | Trianthema protulacastrum | 34.0 | 1.0 (w) | 0 | 3.7 | 1.6 | 0 | 3.0 | 0.4 |

TABLE 1-continued

Inhibition of the microbial growth by the seeds or seed fragments of certain angiospermous plants.

| S. No. | Plant species (family) | Frequency of occurrence on 200 heaps. (%) | Mean weight (mg) of the whole seed (w) or seed fragment (f) tested | Inhibition of the bacterial and fungal growth measured by the parameters: Width of the inhibition zone; ratio of the inhibition zone (mm) and weight of seeds or its fragments (mg) in parenthesis | | | | | |
|---|---|---|---|---|---|---|---|---|---|
| | | | | *1 | 2 | 3 | 4 | 5 | 6 |
| | Aizoaceae (CIMAP 6051) | | | | (3.7) | (1.6) | | (3.0) | (0.4) |
| 48. | *Vigna unguiculata* Pailionaceae (CIMAP 9228) | 0.5 | 81.6 (w) | 1.0 (0.01) | 1.5 (0.018) | 1.0 (0.012) | 7.0 (0.08) | 3.2 (0.03) | 0 |
| 49. | *Xanthium strumarium* Asteraceae (CIMAP 6566) | 0.5 | 2.34 (w) | 0.5 (0.21) | 1.5 (0.64) | 1.2 (0.512) | 5.5 (2.3) | 1.0 (0.4) | 0 |
| 50. | *Zea mays* Poaceae (CIMAP 9211) | 16.0 | 137 (w) | 1.0 (0.007) | 1.0 (0.007) | 1.0 (0.0072) | 5.0 (0.03) | 1.5 (0.01) | 0 |

*1 *Bacillus subtilis*; 2 *Pseudomonas chichorii*; 3 *Salmonella typhimurium*; 4 *Fusarium moniliforme*; 5 *Aspergillus awamori*; 6 *Trichoderma viridis*

What is claimed is:

1. A screening method for the identification of a plant which has antimicrobial activity comprising the following steps in any order:
   a) isolating a plant species growing naturally and surviving on fresh cattle dung or cattle dung which has been decomposing for up to 15 days;
   b) identifying the isolated plant species;
   c) collecting a seed from the identified plant species;
   d) sterilizing the collected seed;
   e) incubating the sterilized seed with a test plate containing (i) a bacterial strain for about 24 hours at 37° C. or (ii) a fungal strain for about 42 hrs at 28° C.;
   f) determining the growth of (i) the bacterial strain or the growth of (ii) the fungal strain in the presence of the seed, wherein a decrease in growth of (i) the bacterial strain or (ii) the fungal strain, is indicative that the seed has antimicrobial activity.

2. The method of claim 1, further determining antimicrobial activity of the seed incubated on the test plate with the bacterial strain or the fungal strain, comprising measuring the radius of bacterial growth inhibition on the test plate and calculating the ratio between the radius of bacterial growth inhibition zone and weight of seed (IZ/SW).

3. The method of claim 1, further comprising testing a second seed from a plant identified in claim 1 for its tolerance to abiotic stress comprising measuring the ability of the second seed to grow under abiotic stress, wherein the ability of the second seed to grow under abiotic stress is indicative that the seed is tolerant to abiotic stress.

4. The method of claim 1, wherein the abiotic stress is a high salt concentration or a paucity of water.

5. A screening method for the identification of a plant which has antimicrobial activity and tolerance to abiotic stresses comprising the following steps in any order:
   a) isolating a plant species growing naturally and surviving on fresh cattle dung or cattle dung which has been decomposing for up to 15 days;
   b) identifying the isolated plant species;
   c) collecting a seed from the identified plant species:
   d) measuring the weight of the seed;
   e) sterilizing the weighed seed;
   f) incubating the sterilized seed with a test plate containing (i) a bacterial strain for about 24 hours at 37° C. or (ii) a fungal strain for about 42 hrs at 28° C.;
   g) determining the growth of (i) the bacterial strain or (ii) the growth of the fungal strain antimicrobial activity wherein a decrease in bacterial growth is indicative that the seed has antimicrobial activity; and
   h) further testing a second seed from step (c) for its ability to tolerate abiotic stresses, wherein growth under abiotic stress is indicative that the seed is tolerant to abiotic stresses.

* * * * *

UNITED STATES PATENT AND TRADEMARK OFFICE
CERTIFICATE OF CORRECTION

PATENT NO. : 6,218,183 B1
DATED : April 17, 2001
INVENTOR(S) : Sushil Kumar et al.

It is certified that error appears in the above-identified patent and that said Letters Patent is hereby corrected as shown below:

Title page,
Item [56], OTHER PUBLICATIONS, "Dhar" delete "Esp" and insert -- Exp --.
Item [57], ABSTRACT,
Delete "novel", "growing on fresh or decomposing bovine cattle dung for", "plants", and insert -- plant --.
Insert -- having -- after plant.

Column 1,
Line 35, delete "," and insert -- ; -- after 91.
Line 38, delete "," and insert -- ; -- after 594.
Line 66, insert -- exhaustively --, original reads "exhaustively"

Column 2,
Line 5, insert -- acetate --, original reads "actate"

Column 3,
Line 27, delete "a" and insert -- and --.

Column 4,
Line 10, delete "sterilising" and insert -- sterilizing --.
Line 34, delete "inherent" and insert -- inharent --.
Line 49, delete "spinocus" and insert -- spinosus --.
Line 57, delete "Ipomea" and insert -- Ipomoea -- .

Column 5,
Line 7, delete "constructed" and insert -- construed --.
Line 56, delete "Nacl" and insert -- NaCl --

Column 6,
Line 13, insert -- 1 -- after "m".
Line 18, delete "for" and insert -- fro --.
Line 49, delete "." after "percent".

UNITED STATES PATENT AND TRADEMARK OFFICE
CERTIFICATE OF CORRECTION

PATENT NO.    : 6,218,183 B1
DATED         : April 17, 2001
INVENTOR(S)   : Sushil Kumar et al.

It is certified that error appears in the above-identified patent and that said Letters Patent is hereby corrected as shown below:

Column 7,
Line 4, delete "finging" and insert -- finding --.
Line 37, delete "<" and insert -- > --.

Tables 2, 3 and 4,
My copies were not clear. Highlighted areas in these tables were not readable.

Table 4,
Delete "caprophilous" and insert -- coprophilous --.

Table 1,
Delete "S." and insert -- S1. --.
1. under column (f) tested "(0.5)"
Under *1 delete "(0.4)" and insert -- (0.5) --

Under 2 delete "(0.25)" and insert -- (0.4) --.
Under 3 delete "(0.75)" and insert -- (0.25) --.
Under 4 delete "(0.5)" and insert -- (0.75) --.
Under 5 insert -- (0.5) --.

6. under column *1 insert -- (0.5) --.
Under 2 delete "(0.5)" and insert -- (0.3) --.
Under 3 delete "(0.3)".
Under 4 insert -- (0.9) --.
Under 5 delete "(0.9)".

10. delete "1.0" and insert -- 1.8 --.

17. delete "Solanceae" and insert -- Solanaceae --.

22. insert -- ( -- before "w".

25. delete "Iopmoea" and insert -- Ipomoea --.

UNITED STATES PATENT AND TRADEMARK OFFICE
CERTIFICATE OF CORRECTION

PATENT NO.   : 6,218,183 B1
DATED        : April 17, 2001
INVENTOR(S)  : Sushil Kumar et al.

It is certified that error appears in the above-identified patent and that said Letters Patent is hereby corrected as shown below:

30. delete "3005" and insert -- 3805 --.

47. delete "protulacastrum" and insert -- portulacastrum --.

48. delete "Pailonaceae" and insert -- Papilionaceae --.

Column 16,
Lines 26 and 27, delete "1" and insert -- 3 --.

Signed and Sealed this

Twenty-first Day of January, 2003

JAMES E. ROGAN
*Director of the United States Patent and Trademark Office*